United States Patent [19]

Kelly

[11] 4,242,268
[45] Dec. 30, 1980

[54] BICYCLIC LACTONES

[75] Inventor: Robert C. Kelly, Kalamazoo, Mich.

[73] Assignee: The Upjohn Company, Kalamazoo, Mich.

[21] Appl. No.: 96,645

[22] Filed: Nov. 23, 1979

Related U.S. Application Data

[62] Division of Ser. No. 654,109, Feb. 2, 1976, abandoned.

[51] Int. Cl.³ .............................................. C07D 307/77
[52] U.S. Cl. .............................. 260/343.3 P; 542/426
[58] Field of Search .................................. 260/343.3 P

[56]       References Cited
          U.S. PATENT DOCUMENTS 3,904,648   9/1975   Kelly .............................. 260/343.3 P

FOREIGN PATENT DOCUMENTS 5018460   2/1975   Japan ................................. 260/343.3 P

*Primary Examiner*—Henry R. Jiles
*Assistant Examiner*—Jane T. Fan

*Attorney, Agent, or Firm*—Robert A. Armitage

[57] ABSTRACT

Process for preparing bicyclic lactone acrylic aldehydes and ketones of the formula

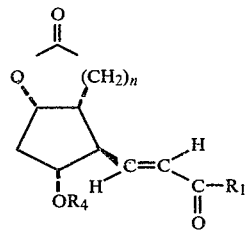

wherein "n" is one or 2, wherein $R_1$ is hydrogen, methyl, or ethyl, and wherein $R_4$ is hydrogen or a blocking group; and those aldehydes, ketones, and intermediates prepared therein. The aldehydes and ketones are useful intermediates in preparing prostaglandins and analogs having pharmacological utility.

2 Claims, No Drawings

BICYCLIC LACTONES

The present application is a divisional application of Ser. No. 654,109, filed Feb. 2, 1976, now abandoned. U.S. Ser. No. 096,806, filed Nov. 23, 1979, is also a divisional application of Ser. No. 654,109.

The present invention relates to prostaglandin analogs, for which the essential material constituting disclosure therefor is incorporated by reference here from U.S. Ser. No. 096,806.

I claim:

1. A compound of the formula

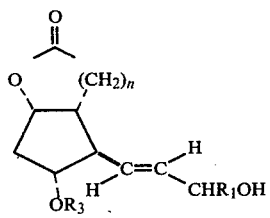

wherein n is one or 2; $R_1$ is hydrogen, methyl, or ethyl; and $R_3$ is a blocking group which is tetrahydropyranyl, tetrahydrofuranyl, or a group of the formula

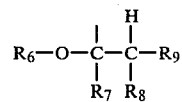

wherein $R_6$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_7$ and $R_8$ are the same or different, being hydrogen, alkyl of one to 4 carbon atoms, inclusive, phenyl or phenyl substituted with one, 2, or 3 alkyl of one to 4 carbon atoms, inclusive, or, when $R_7$ and $R_8$ are taken together, —$(CH_2)a$— or —$(CH_2)b$—O—$(CH_2)c$— wherein a is 3, 4, or 5, b is one, 2, or 3, and c is one, 2, or 3 with the proviso that b plus c is 2, 3, or 4, and wherein $R_9$ is hydrogen or phenyl.

2. A compound according to claim 1 wherein n is one, $R_1$ is hydrogen, and $R_3$ is 1-ethoxyethyl.

* * * * *

UNITED STATES PATENT AND TRADEMARK OFFICE
CERTIFICATE OF CORRECTION

PATENT NO. : 4,242,268
DATED : December 30, 1980
INVENTOR(S) : Robert C. Kelly

It is certified that error appears in the above—identified patent and that said Letters Patent is hereby corrected as shown below:

Column 1, line 11, "U.S. Ser. No. 096,806" should read -- Ser. No. 096,806, now U.S. Patent 4,235,779 --.

Signed and Sealed this

Nineteenth Day of May 1981

[SEAL]

Attest:

RENE D. TEGTMEYER

Attesting Officer        Acting Commissioner of Patents and Trademarks